United States Patent [19]

Karrer et al.

[11] Patent Number: 5,077,311
[45] Date of Patent: Dec. 31, 1991

[54] PEST CONTROL

[75] Inventors: Friedrich Karrer, Zofingen; Alfred Rindlisbacher, Muttenz, both of Switzerland

[73] Assignee: Ciba-Geigy Corporation, Ardsley, N.Y.

[21] Appl. No.: 568,380

[22] Filed: Aug. 16, 1990

Related U.S. Application Data

[63] Continuation of Ser. No. 499,108, Mar. 26, 1990, abandoned.

[30] Foreign Application Priority Data

Mar. 30, 1989 [CH] Switzerland ............. 1162/89

[51] Int. Cl.$^5$ .............................. A01N 47/10
[52] U.S. Cl. ...................................... 514/486
[58] Field of Search ........................ 514/486

[56] References Cited

U.S. PATENT DOCUMENTS 4,215,139 7/1980 Fischer .
4,413,010 11/1983 Zürflüh ........................ 514/486
4,608,389 8/1986 Kisida et al. ................. 514/484

FOREIGN PATENT DOCUMENTS 0004334 10/1979 European Pat. Off. .
2084574 4/1982 United Kingdom .

Primary Examiner—Allen J. Robinson
Attorney, Agent, or Firm—Kevin T. Mansfield; Edward McC. Roberts

[57] ABSTRACT

Use of ethyl 2-[4-(3,5-difluorophenoxy)phenoxy]ethylcarbamate for controlling phytopathogenic insects of the families Aleyrodidae, Diaspididae, Coccidae, Tortricidae and Olethreutidae.

3 Claims, No Drawings

PEST CONTROL

This is a continuation of application Ser. No. 499,108 filed on Mar. 26, 1990, now abandoned.

The present invention relates to the use of ethyl 2-[4-(3,5-difluorophenoxy)phenoxy]ethylcarbamate for controlling phytopathogenic insects of the families Aleyrodidae, Diaspididae, Coccidae, Tortricidae and Olethreutidae. The carbamate used according to the invention is particularly suitable for controlling phytopathogenic representatives of the following families: from the family Aleyrodidae the species *Bemisia tabaci* and *Trialeurodes vaporariorum*, from the families Diaspididae and Coccidae the genera Aonidiella, Quadraspidiotus, Parlatoria and the genera Saissetia and Coccus, from the family Tortricidae the genus Adoxophyes and from the family Olethreutidae the genera Cydia and Lobesia.

EP Application No. 0,004,334 discloses the preparation of alkyl 2-(4-phenoxyphenoxy)ethylcarbamates which are monosubstituted on the phenoxy group, and their use for controlling phytopathogenic insects. GB Patent Specification No. 2,084,574 furthermore describes 2-[4-(phenoxy)phenoxy]ethylcarbamic esters which are alkyl-substituted on the N atom or in the 2-position of the ethylene group, and which are said to be effective, inter alia, as insecticides for controlling phytopathogenic Lepidoptera and Homoptera. U.S. Pat. No. 4,608,389 teaches alkyl 2-[4-(3,5-difluorophenoxy)phenoxy]ethylcarbamates as insecticides, including ethyl 2-[4-(3,5-difluorophenoxy)phenoxy]ethylcarbamate used according to the invention.

In contrast, it has has now been found, surprisingly, that ethyl 2-[4-(3,5-difluorophenoxy)phenoxy]ethylcarbamate, which is known per se from U.S. Pat. No. 4,608,389, in particular is effective in the control of certain phytopathogenic insects. This compound is suitable for controlling whiteflies which are difficult to control (family Aleyrodidae, including, for example, the genera Bemisia and Trialeurodes with the important pest species *Bemisia tabaci* and *Trialeurodes vaporarium*), for controlling scale insects of the families Diaspididae and Coccidae (including, for example, the important genera Aonidiella, Quadraspidiotus, Parlatoria and, for example, the genera Saissetia and Coccus), for controlling caterpillar pests in fruit cultivation of the Tortricidae family (including, for example, the important genus Adoxophyes) and the Olethreutidae family (including, for example, the important genera Cydia and Lobesia). The suitability of the carbamate used according to the invention is to be particularly highlighted for controlling the insect species *Bemisia tabaci, Trialeurodes vaporarium, Aonidiella aurantii, Quadraspidiotus perniciosus, Cydia pomonella, Adoxophyes reticulana* and *Lobesia botrana*.

Ethyl 2-[4-(3,5-difluorophenoxy)phenoxy]ethylcarbamate used according to the invention acts on the abovementioned pests essentially as a chemosterilant, an ovicide and a population or metamorphosis inhibitor.

The carbamic ester used according to the invention can be prepared analogously to the process described in U.S. Pat. No. 4,608,389 (cf. Example 1 below):

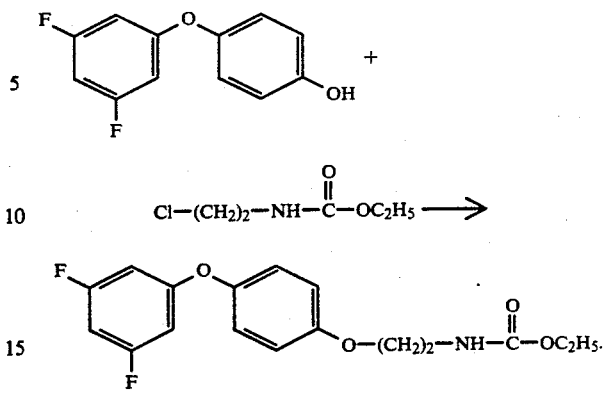

The insecticidal action of ethyl 2-[4-(3,5-difluorophenoxy)phenoxy]ethylcarbamate can be considerably broadened and adapted to given circumstances by adding other insecticides and/or acaricides. Examples of suitable additions are organophosphorus compounds; nitrophenols and their derivatives; formamides; ureas; pyrethrin-type compounds, and also carbamates and chlorinated hydrocarbons.

The good pesticidal action of ethyl 2-[4-(3,5-difluorophenoxy)phenoxy]ethylcarbamate corresponds to an achieved destruction rate (mortality) of at least 50-60% of the above-mentioned harmful insects to be controlled.

Ethyl 2-[4-(3,5-difluorophenoxy)phenoxy]ethylcarbamate used according to the invention is employed in unaltered form or, preferably, together with the auxiliaries conventionally used in the art of formulation, and it is therefore processed in a known manner to give, for example, emulsion concentrates, directly sprayable or dilutable solutions, dilute emulsions, wettable powders, soluble powders, dusts, granules, and also encapsulations, for example in polymeric substances. The application methods, such as spraying, misting, atomizing, scattering or watering, as well as the nature of the agents, are selected to suit the intended aims and the prevailing circumstances.

The formulations to be used according to the invention, i.e. the agents, preparations or compositions containing the insecticidal active substance and, if desired, a solid or liquid additive, are prepared in a known manner, for example by intimately mixing and/or grinding the active substances with extenders, for example with solvents, solid carriers, and, if desired, surface-active compounds (surfactants).

The following may be suitable as solvents: aromatic hydrocarbons, preferably the fractions $C_8$ to $C_{12}$, for example xylene mixtures or substituted naphthalenes, phthalic esters, such as dibutyl phthalate or dioctyl phthalate, aliphatic hydrocarbons, such as cyclohexane or paraffins, alcohols and glycols, as well as their ethers and esters, such as ethanol, ethylene glycol, ethylene glycol monomethyl ether or ethylene glycol monoethyl ether, ethyl acetate, propyl myristate or propyl palmitate, ketones, such as cyclohexanone, strongly polar solvents, such as N-methyl-2-pyrrolidone, dimethyl sulfoxide or dimethylformamide, and epoxidized or unepoxidized vegetable oils, such as epoxidized coconut oil or soya oil; silicone oils or water.

Solid carriers, for example dusts and dispersible powders, which are generally used are natural ground minerals, such as calcite, talc, kaolin, montmorillonite or attapulgite. To improve the physical properties, it is also possible to add highly-disperse silica or highly-disperse absorptive polymers. Suitable particulate adsorptive granulate carriers are porous types, for example pumice, brick grits, sepiolite or bentonite, and examples of non-sorptive carriers are calcite or sand. In addition, a large number of pregranulated materials of inorganic or organic nature can be used, such as, in particular, dolomite or comminuted plant residues.

Possible surface-active compounds, depending on the type of the intended formulation, are non-ionic, cationic and/or anionic surfactants having good emulsifying, dispersing and wetting properties. Surfactants are also understood as meaning mixtures of surfactants.

Suitable anionic surfactants can be so-called water-soluble soaps as well as water-soluble synthetic surface-active compounds.

Soaps which are suitable are the alkali metal salts, alkaline earth metal salts or substituted or unsubstituted ammonium salts of higher fatty acids ($C_{10}$–$C_{22}$), for example the Na or K salts of oleic or stearic acid, or of natural mixtures of fatty acids, as can be obtained, for example, from coconut oil or tall oil. Furthermore, mention must also be made of the fatty acid methyltaurinates.

However, so-called synthetic surfactants are used more frequently, in particular fatty sulfonates, fatty sulfates, sulfonated benzimidazole derivatives or alkylarylsulfonates.

The fatty sulfonates or fatty sulfates are generally present in the form of alkali metal salts, alkaline earth metal salts or substituted or unsubstituted ammonium salts and have an alkyl radical having 8 to 22 C atoms, alkyl also including the alkyl moiety of acyl radicals, for example the Na or Ca salt of ligninsulfonic acid, of the dodecylsulfuric ester or of a fatty alcohol sulfate mixture prepared from natural fatty acids. This section also includes the salts of the sulfuric esters and sulfonic acids of fatty alcohol/ethylene oxide adducts. The sulfonated benzimidazole derivatives preferably contain 2 sulfonyl groups and one fatty acid radical having 8–22 C atoms. Examples of alkylarylsulfonates are the Na, Ca or triethanolamine salts of dodecylbenzenesulfonic acid, of dibutylnaphthalenesulfonic acid, or of a naphthalenesulfonic acid/formaldehyde condensation product.

Other suitable substances are also the corresponding phosphates, for example salts of the phosphoric ester of a p-nonylphenol/(4–14)-ethylene oxide adduct, and phospholipids.

Suitable non-ionic surfactants are mainly polyglycol ether derivatives of aliphatic or cycloaliphatic alcohols, of saturated or unsaturated fatty acids and of alkylphenols, and these derivatives can contain 3 to 30 glycol ether groups and 8 to 20 carbon atoms in the (aliphatic) hydrocarbon radical and 6 to 18 carbon atoms in the alkyl radical of the alkylphenols.

Other suitable non-ionic surfactants are the water-soluble polyethylene oxide adducts with polypropylene glycol, ethylene diaminopolypropylene glycol and alkylpolypropylene glycol which have 1 to 10 carbon atoms in the alkyl chain and which contain 20 to 250 ethylene glycol ether groups and 10 to 100 propylene glycol ether groups. The compounds mentioned generally contain 1 to 5 ethylene glycol units per propylene glycol unit.

Examples of non-ionic surfactants which may be mentioned are nonylphenol polyethoxyethanols, castor oil polyglycol ether, castor oil thioxilate, polypropylene/polyethylene oxide adducts, tributylphenoxypolyethoxyethanol, polyethylene glycol and octylphenoxypolyethoxyethanol.

Fatty acid esters of polyoxyethylene sorbitan, such as polyoxyethylene sorbitan trioleate, are furthermore also suitable.

The cationic surfactants are mainly quaternary ammonium salts which contain at least one alkyl radical having 8 to 22 C atoms as the N substituent and which have lower, halogenated or free alkyl radicals, benzyl radicals or lower hydroxyalkyl radicals as further substituents. The salts are preferably in the form of halides, methylsulfates or ethylsulfates, for example stearyltrimethylammonium chloride or benzyldi(2-chloroethyl)ethylammonium bromide.

The surfactants customary in the art of formulation are described, inter alia, in the following publications: "McCutcheon's Detergents and Emulsifiers Annual" MC Publishing Corp., Ridgewood, N.J. 1979; Dr. Helmut Stache "Tensid Taschenbuch" [Surfactant Guide], Carl Hanser Verlag Munich/Vienna 1981.

The insecticidal preparations used according to the invention generally contain 0.1 to 99%, in particular 0.1 to 95%, of ethyl 2-[4-(3,5-difluorophenoxy)phenoxy]ethylcarbamate, 1 to 99.9% of a solid or liquid additive and 0 to 25%, in particular 0.1 to 25%, of a surfactant, % meaning percent by weight. While concentrated agents tend to be preferred as commercially available goods, the end user generally uses dilute agents or preparations having considerably lower concentrations of active substance, for example 0.1 to 1,000 ppm. The application rate of the active substance to be used according to the invention is—in particular for agricultural areas—generally 0.025 to 1.0 kg/ha, preferably 0.1 to 0.5 kg/ha, for example 0.1 to 0.25 kg/ha.

The abovementioned agents can also contain further additions, such as stabilizers, defoamers, viscosity regulators, binders, tackifiers as well as fertilizers or other active substances for obtaining specific effects.

EXAMPLE 1

Preparation of ethyl 2-[4-(3,5-difluorophenoxy)phenoxy]ethylcarbamate 27.6 g of finely-pulverulent potassium carbonate, 18.2 g of ethyl 2-chloroethylcarbamate and 1 g of powdered potassium iodide are added to a solution of 22.2 g of 4-(3,5-difluorophenoxy)phenol in 80 ml of dimethylformamide. The reaction mixture is heated for 16 hours at 95° C., with stirring. After this, the reaction mixture is filtered, the filtrate is poured into 400 ml of water, and the mixture is extracted repeatedly with diethyl ether. The combined organic phases are washed with water and dried over sodium sulfate, and the solvent is distilled off. The residue is purified by chromatography over silica gel (eluent: n-hexane/diethyl ether 3:1), which gives the pure ethyl 2-[4-(3,5-difluorophenoxy)-phenoxy]ethylcarbamate as a colourless compound which soon crystallizes and has a melting point of 54°–56° C. The $^1$H-NMR spectrum agrees with the indicated structure.

EXAMPLE 2

Contact Action against *Bemisia tabaci*

Potted dwarf-bean plants (untreated) are infested with *Bemisia tabaci* (Whitefly; 40 unsexed adults per plant). The test animals are kept on the plants by means of plastic cylinders. After eggs have been laid for two days, all the adults which are present are removed. Ten days after the adults have been removed, i.e., at a point in time when approximately 80% of the nymphs are in the second nymph stage, the infested plants are sprayed to run off point with an aqueous emulsion preparation of the active substance to be tested (concentration 10 ppm). 14 days after the active substance has been applied, the test is evaluated for % hatch reduction (=% action) compared with untreated control batches. The experiment is carried out in a climatized chamber at 26° C., a relative atmospheric humidity of approximately 50% and a 14-hour photoperiod (10,000 Lux).

In this test, ethyl 2-[4-(3,5-difluorophenoxy)phenoxy]ethylcarbamate shows a 100% activity.

EXAMPLE 3

Action against *Aonidiella aurantii* (Immersion Test—Potato Tubers)

Small potato tubers are infested with crawlers of *Aonidiella aurantii* (orange scale) in such a way that the potatoes are kept in direct contact with large pumpkins heavily infested with Anodiella, for a period of about 24 hours, so that eventually each potato is infested with 200 to 300 crawlers. When after about two weeks the larvae have settled on the potatoes and have undergone ecdysis for the first time ($L_2$ stage), the potatoes are immersed by means of tongs for about 2 to 3 minutes in an aqueous emulsion preparation which contains the active substance to be tested in a concentration of 10 ppm. After the potato tubers which have been treated in such a way have dried, they are transferred for a period of 10 to 12 weeks to plastic containers which are provided, in the upper part, with a glue ring which serves for trapping the winged males. After this, the state of the treated scale-insect population is evaluated by comparing it with that of untreated control batches, the evaluation being carried out by scoring the number of crawlers of the first consecutive generation (% action).

The test is carried out in a climatized chamber at 26° C., 50% relative atmospheric humidity under a 14-hour photoperiod (10,000 Lux).

In this test, ethyl 2-[4-(3,5-difluorophenoxy)phenoxy]ethylcarbamate shows a 100% activity.

EXAMPLE 4

Ovicidal action on *Cydia pomonella*, *Adoxophyes reticulana* and *Lobesia botrana*

Eggs of the above fruit pests, which are not older than 24 hours and which have been deposited on paper strips, are cut out in such a manner that about 50 eggs of one species of pest are present per paper cutting. These paper cuttings together with the eggs are now immersed three times for a few seconds in an aqueous emulsion preparation containing 5 ppm of the active substance to be tested. After the test formulation has dried on, the eggs are placed in Petri dishes (5 cm diameter) and kept at a temperature of about 26° C., 80% relative atmospheric humidity and a photoperiod of 14 hours (about 2,000 Lux). In the case of *Cydia pomonella* (Codling moth), the treated egg clusters are deposited in the Petri dish between two round paper filters. In the case of *Adoxophyes reticulana* (summer fruit Tortrix moth) and of *Lobesia botrana* (grape berry moth), the egg clusters are deposited under the lid of the Petri dish between two round fabric filters, the bottom of the Petri dish being covered with a normal diet for Lepidoptera. After 6 days, the hatch percentage of larvae from the treated eggs is evaluated by comparison with untreated control batches (% hatch reduction).

In the above test, ethyl 2-[4-(3,5-difluorophenoxy)phenoxy]ethylcarbamate shows an 80-100% activity against the pests mentioned.

EXAMPLE 5

Insecticidal Formulations of the Active Substance Ethyl 2-[4-(3,5-difluorophenoxy)phenoxy]ethylcarbamate (%=percent by weight)

| 1. Wettable powder | a) | b) | c) |
| --- | --- | --- | --- |
| Active substance | 20% | 50% | 75% |
| Na ligninsulfonate | 5% | 5% | — |
| Na laurylsulfate | 3% | — | 5% |
| Na diisobutylnaphthalene-sulfonate | — | 6% | 10% |
| Octylphenol polyethylene glycol ether (7-8 mol of EO) | — | 2% | — |
| Highly disperse silica | 5% | 10% | 10% |
| Kaolin | 67% | 27% | — |

The active substance is mixed with the additives and the mixture is ground thoroughly in a suitable mill. This gives wettable powders which can be diluted with water to give suspensions of any desired concentration.

| 2. Emulsion concentrate | a) | b) |
| --- | --- | --- |
| Active Substance | 10% | 10% |
| Octylphenol polyethylene glycol ether (4-5 mol of EO) | 3% | — |
| Ca dodecylbenzenesulfonate | 3% | — |
| Castor oil polyglycol ether (36 mol of EO) | 4% | — |
| Castor oil thioxilate | — | 25% |
| Cyclohexanone | 30% | — |
| Butanol | — | 15% |
| Xylene mixture | 50% | — |
| Ethyl acetate | — | 50% |

Emulsions of any desired concentration can be prepared from this concentrate by dilution with water.

| 3. Dusts | a) | b) |
| --- | --- | --- |
| Active substance | 5% | 8% |
| Talc | 95% | — |
| Kaolin | — | 92% |

Ready-to-use dusts are obtained by mixing the active substance with the carrier and grinding the mixture on a suitable mill.

| 4. Extruder granules | |
| --- | --- |
| Active substance | 10% |
| Na ligninsulfonate | 2% |
| Carboxymethylcellulose | 1% |
| Kaolin | 87% |

The active substance is mixed with the additives, and the mixture is ground and moistened with water. This mixture is extruded and then dried in a stream of air.

| 5. Coated granules | |
| --- | --- |
| Active substance | 3% |

| 5. Coated granules | |
| --- | --- |
| Polyethylene glycol (MW 200) | 3% |
| Kaolin | 94% |

In a mixer, the kaolin which is moistened with polyethylene glycol is coated uniformly with the finely-ground active substance. This gives dust-free coated granules.

| 6. Suspension concentrate | |
| --- | --- |
| Active substance | 40% |
| Ethylene glycol | 10% |
| Nonylphenol polyethylene glycol ether (15 mol of EO) | 6% |
| Na ligninsulfonate | 10% |
| Carboxymethylcellulose | 1% |
| 37% aqueous formaldehyde solution | 0.2% |
| Silicone oil in the form of a 75% aqueous emulsion | 0.8% |

| 6. Suspension concentrate | |
| --- | --- |
| Water | 32% |

The finely ground active substance is mixed intimately with the additives. This gives a suspension concentrate from which suspensions of any desired concentration can be prepared by dilution with water.

We claim:

1. A method of controlling phytopathogenic insects of the families Aleyrodidae, Diaspididae, Coccidae, Tortricidae and Olethreutidae, which comprises treating said insects or various development stages thereof or their habitat, with an insecticidally effective amount of ethyl 2-[4-(3,5-difluorophenoxy)phenoxy]-ethylcarbamate or wtih a composition containing an insecticidally effective amount of this compound as active ingredient, and a carrier therefor or other adjuvant.

2. A method according to claim 1 for controlling insects of the genera Bemisia, Trialeurodes, Aonidiella, Quadraspidiotus, Parlatoria, Saissetia, Coccus, Adoxophyes, Cydia and Lobesia.

3. A method according to claim 2 for controlling *Bemisia tabaci, Trialeurodes vaporarium, Aonidiella aurantii, Quadraspidiotus perniciosus, Cydia pomonella, Adoxophyes reticulana* and *Lobesia botrana*.

* * * * *